(12) United States Patent
Tsukuma et al.

(10) Patent No.: US 7,888,279 B2
(45) Date of Patent: Feb. 15, 2011

(54) HIGH TOUGHNESS TRANSLUCENT ALUMINA SINTERED BODY, METHOD FOR PRODUCING THE SAME, AND ITS USES

(75) Inventors: Koji Tsukuma, Kanagawa (JP); Isao Yamashita, Kanagawa (JP); Hitoshi Nagayama, Tokyo (JP)

(73) Assignee: Tosoh Corporation, Shunan-Shi, Yamaguchi (JP)

( * ) Notice: Subject to any disclaimer, the term of this patent is extended or adjusted under 35 U.S.C. 154(b) by 119 days.

(21) Appl. No.: 12/289,425

(22) Filed: Oct. 28, 2008

(65) Prior Publication Data

US 2009/0111067 A1 Apr. 30, 2009

(30) Foreign Application Priority Data

Oct. 30, 2007 (JP) ............................. 2007-281926

(51) Int. Cl.
*C04B 35/115* (2006.01)
(52) U.S. Cl. .......................................... 501/153; 433/8
(58) Field of Classification Search ................ 501/153; 433/8
See application file for complete search history.

(56) References Cited

U.S. PATENT DOCUMENTS

| | | | |
|---|---|---|---|
| 3,026,210 A | | 3/1962 | Coble et al. |
| 4,204,874 A | * | 5/1980 | Yamada ........................ 501/153 |
| 4,952,537 A | | 8/1990 | Hayashi et al. |
| 5,096,862 A | * | 3/1992 | Mathers et al. ............. 501/96.1 |
| 5,109,586 A | * | 5/1992 | Jones et al. ............... 29/896.11 |
| 6,143,678 A | * | 11/2000 | Yamamoto et al. .......... 501/128 |
| 6,417,127 B1 | | 7/2002 | Yamamoto et al. |
| 6,482,761 B1 | * | 11/2002 | Watanabe et al. ............ 501/153 |
| 6,648,638 B2 | | 11/2003 | Castro et al. |
| 6,680,268 B2 | * | 1/2004 | Alford et al. ................. 501/127 |
| 6,734,128 B2 | * | 5/2004 | Asano ......................... 501/153 |
| 6,878,456 B2 | | 4/2005 | Castro et al. |

(Continued)

FOREIGN PATENT DOCUMENTS

EP 0430654 A1 11/1990

(Continued)

OTHER PUBLICATIONS

Y. Yoshizawa et al., Preparation of High Fracture Toughness Alumina Sintered Bodies from Bayer Aluminum Hydroxide, Journal of the Ceramic Society of Japan, 1998, pp. 1172-1177, vol. 106.

*Primary Examiner*—Karl E Group
(74) *Attorney, Agent, or Firm*—Westerman, Hattori, Daniels & Adrian, LLP

(57) ABSTRACT

In the conventional alumina sintered bodies, a sintered body having high flexural strength, high toughness and high translucency in combination is not obtained, and a translucent alumina sintered body suitable for a dental material requiring both strength and sensuousness was not obtained. A translucent alumina sintered body having fracture toughness of 4.5 MPa·m$^{0.5}$ or more, flexural strength of 350 MPa or more, and all light transmittance (sample thickness: 1 mm) to a visible light having a wavelength of 600 nm, of 60% or more is provided. The sintered body wherein sintered crystal grains are slender plate-like and/or columnar shape having an average aspect ratio of 1.5 or more and an average long axis length of 15 μm or less is preferred.

6 Claims, 5 Drawing Sheets

U.S. PATENT DOCUMENTS

| | | | |
|---|---|---|---|
| 7,247,591 B2 * | 7/2007 | Wei | 501/153 |
| 2003/0125189 A1 * | 7/2003 | Castro et al. | 501/127 |
| 2003/0165790 A1 * | 9/2003 | Castro et al. | 433/8 |
| 2006/0211568 A1 * | 9/2006 | Wei | 501/153 |
| 2007/0027026 A1 * | 2/2007 | Rhodes et al. | 501/153 |
| 2007/0194503 A1 * | 8/2007 | Wei | 264/647 |
| 2007/0259303 A1 | 11/2007 | Tsukuma et al. | |
| 2009/0137380 A1 * | 5/2009 | Bernard-Granger et al. | 501/125 |

FOREIGN PATENT DOCUMENTS

| | | |
|---|---|---|
| JP | 63-236757 A | 10/1988 |
| JP | 03-168140 A | 7/1991 |
| JP | 03-261648 A | 11/1991 |
| JP | 2001-322866 A | 11/2001 |
| JP | 2006-087915 A | 4/2006 |
| WO | 2007074298 * | 7/2007 |

* cited by examiner

HIGH TOUGHNESS TRANSLUCENT ALUMINA SINTERED BODY, METHOD FOR PRODUCING THE SAME, AND ITS USES

FIELD OF THE INVENTION

The present invention relates to an alumina sintered body suitable for a dental material such as an orthodontic bracket or a mill blank for artificial denture, due to high toughness, improved brittleness and excellent translucency.

BACKGROUND OF THE INVENTION

Regarding a translucent alumina and its production method, a high temperature sintering method in hydrogen or vacuum atmosphere, a pressure sintering method using HIP or the like, and the like are conventionally known.

Regarding the former, there are many reports such as a method of adding a grain growth inhibitor such as MgO to an alumina powder and sintering the mixture at high temperature of 1,600° C. or more in a hydrogen-containing atmosphere or a vacuum atmosphere (for example, see Patent Document 1). In this method, a translucent alumina having flexural strength of from 300 to 400 MPa comprising large crystal grains having a grain size of from about 20 to 50 μm is produced.

On the other hand, the latter method is a method of pressureless sintering a high purity alumina powder and highly densifying the same with HIP treatment to impart translucency (see Patent Documents 2 to 8). In this method, a sintering temperature of 1,500° C. or lower is used. Therefore, a sintered body comprising fine grains of from about 0.5 to 5 μm can be produced, and a translucent alumina having high flexural strength of 500 MPa or more is obtained. Furthermore, there is reported that by decreasing the grain size to 2 μm or less, flexural strength (about 800 MPa) which is about two times that of the translucent alumina produced by the conventional high temperature sintering method is obtained (see Patent Documents 2, 4, 5 and 8). However, those translucent aluminas have high flexural strength, but had the problem that fracture toughness is low, and therefore the alumina is brittle and is liable to get chipped. For example, Patent Document 3 reports a low fracture toughness value of from 3 to 4 MPa·m$^{0.5}$.

A high toughness sintered body having fracture toughness of from about 5 to 9 MPa·m$^{0.5}$, which is a sintered body having an anisotropy in grain shape and comprises slender grains is reported as an alumina sintered body having high fracture toughness (Non-Patent Document 1). However, this sintered body has high toughness but did not have translucency. The reason for this is considered that the presence of impurities and/or additives of from 500 to several thousand ppm is necessary in the conventional sintered body of anisotropic grains, and this impairs sintering properties. For example, the case that when additives are added to a high purity translucent alumina by HIP pressure sintering method to form slender anisotropic crystal grains, the sintered bodies are opaque is reported in Patent Document 5, and it is indicated that anisotropic grains do not result in translucency.

There are only the reports that a translucent alumina by the conventional HIP pressure sintering method comprises isotropic crystal grains, and this is apparent from texture photographs of sintered body in the reports up to now (see Patent Documents 3 to 8).

Thus, in the conventional non-pressure high temperature sintering method, only a translucent alumina of low strength and low toughness is obtained, and in the HIP pressure sintering method, only a translucent alumina of low toughness although high strength is obtained. Thus, an alumina sintered body having high strength/high toughness and high translucency in combination was not obtained.

Patent Document 1: U.S. Pat. No. 3,026,210
Patent Document 2: JP-A-63-236757
Patent Document 3: JP-A-3-168140
Patent Document 4: JP-A-3-261648
Patent Document 5: JP-A-2001-322866
Patent Document 6: U.S. Pat. No. 6,878,456
Patent Document 7: U.S. Pat. No. 6,648,638
Patent Document 8: JP-A-2006-87915
Non-Patent Document 1: J. Ceram. Soc. Jpn., 106 [12], pp. 1172-77 (1998)

SUMMARY OF THE INVENTION

The present invention relates to an alumina sintered body having high toughness, high strength and high translucency. The present translucent alumina sintered body can widely be utilized not only as a lamp tube such as a sodium lamp or a metal halide lamp, but as a dental material such as an orthodontic bracket, a mill blank for dental prosthesis, or crown and bridge for dental restoration. In particular, in the uses of a dental material such as an orthodontic bracket or a mill blank for dental prosthesis, flexural strength and fracture toughness as resistance force that can prevent fracture, crack or the like under operating stress are necessary in addition to translucency required from the aesthetic standpoint. The present invention provides an alumina sintered body having all of those properties.

As a result of earnest studies on the improvement of translucency and strength (flexural strength and fracture toughness) of an alumina sintered body, the present inventors have found that an alumina sintered body containing specific additives in a specific concentration range becomes a new translucent alumina sintered body having all of high translucency, high flexural strength and high fracture toughness. In particular, they have found that when constituting crystal grains have an anisotropic shape, fracture toughness is excellent without impairing translucency, and have reached to complete the present invention.

That is, the present invention provides a translucent alumina sintered body having fracture toughness of 4.5 MPa·m$^{0.5}$ or more, flexural strength of 350 MPa or more, and all light transmittance (sample thickness: 1 mm) to a visible light having a wavelength of 600 nm, of 60% or more.

Further, the present invention provides a method for producing a translucent alumina sintered body, comprising molding an alumina powder having a purity of 99.95% or more with at least one selected from the group consisting of silicon oxide, boron oxide, phosphorus oxide, germanium oxide, Group 1A alkali metal oxides, and Group 2A alkaline earth metal oxides other than MgO in the total amount of from 20 to 400 ppm, pressureless sintering the resulting molded article, and subjecting the resulting sintered body to a hot isostatic press treatment.

DETAILED DESCRIPTION OF THE INVENTION

Figure 1:
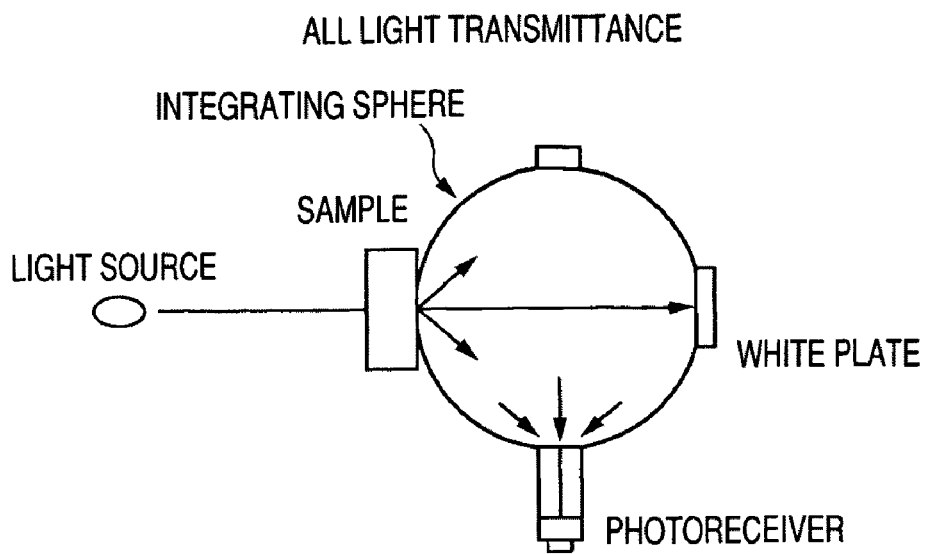
FIG. 1 is a schematic view of all light transmittance measurement apparatus.

The translucent alumina sintered body of the present invention is described below.

The translucent alumina sintered body of the present invention is a translucent alumina sintered body having fracture toughness of 4.5 $MPa \cdot m^{0.5}$ or more, a flexural strength of 350 MPa or more, and all light transmittance (sample thickness: 1 mm) to a visible light having a wavelength of 600 nm, of 60% or more.

The fracture toughness is 4.5 $MPa \cdot m^{0.5}$ or more, and it is preferred to be particularly 5.0 $MPa \cdot m^{0.5}$ or more, and further 6.0 $MPa \cdot m^{0.5}$ or more. The flexural strength is 400 MPa or more, and it is preferred to be particularly 500 MPa or more, and further 600 MPa or more. The evaluation methods of fracture toughness and flexural strength used herein are the methods defined in JIS R1607 and JIS R1601, respectively.

The sintered body of the present invention has high all light transmittance to a visible light of 600 nm of 60% or more in a sample thickness of 1 mm, and it is preferred to be particularly 65% or more, and further 70% or more.

The translucent alumina sintered body of the present invention preferably contains 99.95% or more of aluminum oxide, and as other additives, at least one selected from the group consisting of silicon oxide, boron oxide, phosphorus oxide, germanium oxide, Group 1A alkali metal oxides, and Group 2A alkaline earth metal oxides other than MgO in the total amount of from 20 to 400 ppm. Group 1A alkali metals include lithium (Li), sodium (Na), potassium (K), rubidium (Rb), cesium (Cs), and francium (Fr). Group 2A alkaline earth metals include beryllium (Be), magnesium (Mg), calcium (Ca), strontium (Sr), barium (Ba), and radium (Ra).

Those additives form a glass phase in an alumina sintered body, and the particularly preferred example includes the combination of sodium oxide and silicon oxide. On the other hand, of the Group 2A alkaline earth metal oxides, MgO is a grain growth inhibitor and is therefore excluded. Furthermore, there is the case that CaO is not used depending on the co-presence state of other elements.

Where the content of those additives is less than 20 ppm, its effect is not obtained, and where the content exceeds 400 ppm, densification is impaired, and the translucency is liable to be fallen outside the scope of the present invention. Therefore, the allowable range of the content is from 20 to 400 ppm, and more preferably 30 to 150 ppm. MgO acting as a grain growth inhibitor is not contained at all, or even if contained in a level of impurities, the content is preferably less than 20 ppm.

The above-described additives have the action to suppress grain growth at low sintering temperature, and have the action to promote anisotropic growth grains to make sintered crystal grains have a slender shape at high sintering temperature. Therefore, the additives have the effect to form a sintered body having high toughness.

The translucent alumina sintered body of the present invention is preferably that sintered crystal grains are slender plate-like and/or columnar shape having an average aspect ratio of 1.5 or more and an average long axis length of 15 μm or less. Where the average aspect ratio is less than 1.5, it is difficult to achieve fracture toughness of 4.5 $MPa \cdot m^{0.5}$ or more. When it is 1.5 or more, it can be recognized as apparently being an anisotropic slender shape. For example, Patent Document 5 exemplifies from 1.3 to 1.4 as an aspect ratio of a translucent alumina comprising isotropic grains.

Figure 2:
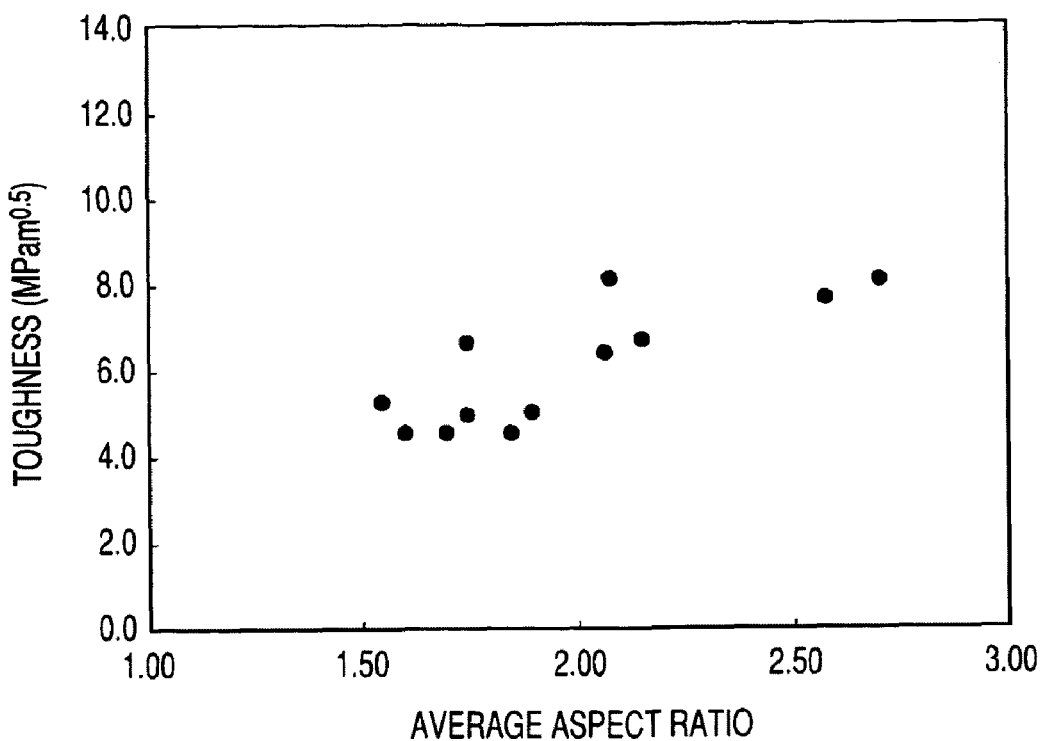
FIG. 2 is a correlation between an average grain aspect ratio and fracture toughness.

The relationship between an average aspect ratio and fracture toughness of the alumina sintered body of the present invention is shown in FIG. 2, and examples of the grain shape of the alumina sintered body of the present invention are shown in FIGS. 3, 4, 6 and 7. Fracture toughness is increased with the increase of the average aspect ratio, and the fracture toughness can be 10 $MPa \cdot m^{0.5}$ or more. In such a case, flexural strength tends to be decreased. From the standpoint of toughness and strength in combination, the average aspect ratio is preferably from 1.6 to 2.2, and in this range, high toughness and high strength that the fracture toughness is 5.0 $MPa \cdot m^{0.5}$ or more and the flexural strength is 400 MPa or more are obtained.

The average long axis length of the sintered crystal grains of the present invention is preferably 15 μm or less. Even where exceeding 15 μm, high fracture toughness can be achieved, but flexural strength is liable to be decreased. From the standpoint of toughness and strength in combination, it is preferred that the average long axis length is more than 1 μm, particularly from 1.2 to 6.0 μm, and further from 1.7 to 3.2 μm.

Conventionally, it was considered that a sintered body comprising slender grains having a large aspect ratio is opaque and does not show translucency as described in Patent Document 5. Furthermore, it was considered that even in a translucent alumina by a high temperature sintering method, translucency is not obtained unless the generation of slender abnormal growth grains is suppressed by the addition of a grain growth inhibitor such as MgO to form grains having isotropic shape (Patent Document 1). However, in the conventional sintered body, densification is difficult to proceed when anisotropic growth grains are generated, and pores remain in the sintered body. Thus, translucency was not obtained. In the sintered body of the present invention, grain growth inhibition effect and anisotropic growth promotion effect are obtained according to the sintering temperature in the kind of specific additives and the range of the addition amount thereof, the aspect ratio of sintered crystals can be controlled in the state free from adverse influence to densification, and a sintered body excellent in all of fracture toughness, flexural strength and translucency is obtained.

A method for producing a translucent sintered body is described below.

The translucent alumina sintered body of the present invention can be produced by molding a mixture of an alumina powder having a purity of 99.99% or more and at least one selected from the group consisting of silicon oxide, boron oxide, phosphorus oxide, germanium oxide, Group 1A alkali metal oxides, and Group 2A alkaline earth metal oxides other than MgO in the total amount of from 20 to 400 ppm, pressureless sintering the resulting molded article to obtain a primary sintered body, and subjecting the resulting sintered body to a hot isostatic press treatment.

The alumina powder is not particularly limited so long as the purity of the present invention is satisfied. For example, the commercially available powder having a purity of 99.99% or more (for example, products manufactured by Taimei Chemicals Co., Ltd., or products manufactured by Sumitomo Chemical Co., Ltd.) can be used.

Oxides of at least one of the group of silicon oxide, boron oxide, phosphorus oxide, germanium oxide, Group 1A alkali metal oxides, and Group 2A alkaline earth metal oxides other than MgO as additives are dispersed in and mixed with, for example, the alumina powder using a mixing and crushing apparatus. Those additives are not always necessary to be added as an oxide, and precursors that convert into oxides by thermal decomposition may be added. Components (precursors) contained in an organic binder for molding can also be utilized. For example, in the case of $SiO_2$, a silica powder or an organosilicon compound such as silicon alkoxide or silicone is exemplified, and in the case of $Na_2O$, a sodium salt such as $Na_2CO_3$, an organic complex such as sodium stearate, or sodium silicate is exemplified.

The primary sintered body is produced by sintering a powder molded article in an atmosphere of air, oxygen, vacuum of the like. The simplest atmosphere is air. The sintering temperature is required to increase until a relative density is 95% or more. The reason for this is that a high pressure gas is avoided from being permeated in the inside of a sintered body in the subsequent HIP treatment.

A size of sintered crystal grains of the primary sintered body is preferably small as possible, and is preferably less than about 5 μm. Where the sintered crystal grain size of the primary sintered body is 5 μm or more, translucency of the alumina sintered body obtained is liable to be decreased.

Whether or not the primary sintered body becomes translucent when subjected to HIP treatment is determined by a grain size of the primary sintered body. Plastic flow of grains becomes active under high temperature and high pressure of HIP as the grain size is small, and extinction of residual pores is promoted. In the present invention, by adding the above-described additives to a high purity alumina, the grain size of the primary sintered body is controlled to be small, and translucency can be enhanced by HIP treatment.

For example, when the commercially available high purity alumina powder (product manufactured by Taimei Chemicals Co., Ltd.) is used and sintered at 1,400° C., the grain size is 2.9 μm when the additive was not added, and the grain size is 1.0 μm when $NaSiO_3$ was added in an amount of 100 ppm. Mechanism of this grain growth inhibition effect is not always clarified, but it is considered that a hetero-phase containing additives is formed at the grain boundary, and this constitutes a barrier of grain growth.

It is preferred that the sintering temperature is set as low as possible in order to decrease a grain size of the primary sintered body as possible, and it is preferred to set to a temperature capable of adjusting a relative density to from 95 to 98%. The sintering temperature is preferably from 1,250 to 1,400° C., and particularly from 1,250 to 1,350° C.

The HIP treatment is conducted for the purpose of extinguishing residual pores in the sintered body and imparting translucency. The purpose can be achieved by a treatment temperature of 1,200° C. or higher and a treatment pressure of 50 MPa or more. In the present invention, a temperature of from 1,350 to 1,550° C. is preferred. Where the temperature is lower than 1,350° C., anisotropic growth is insufficient, and it is difficult to form grains having a small aspect ratio. Where the temperature is higher than 1,550° C., anisotropic growth proceeds too much, coarse grains having a long axis length exceeding 15 μm are increased, and flexural strength is liable to be decreased.

The HIP treatment promotes anisotropic grain growth of sintered body. For example, an average aspect ratio of 1,450° C. pressureless sintered body having added thereto 100 ppm of $Na_2O.SiO_2$ is 1.4. However, when the HIP treatment is conducted at the same temperature, the ratio is 2.1. Thus, anisotropic growth is promoted by the HIP treatment.

As a pressure medium in HIP can be used an argon gas generally used. Other gases such as nitrogen or oxygen can be used. The pressure is 50 MPa or more, and when the pressure is from 100 to 200 MPa generally used, a sufficient effect is obtained.

The sintered body of the present invention has both high toughness and high translucency, and is suitable as a dental material, in particular, a material used in an orthodontic bracket or a mill blank for dental prosthesis.

Conventionally, translucent alumina used as a bracket is produced by a high temperature sintering method, and comprises grains of 20 μm or more. Therefore, the alumina has flexural strength of from 300 to 400 MPa, but fracture toughness was merely from about 3 to 4 $MPa \cdot m^{0.5}$.

The translucent alumina produced by the conventional HIP pressure sintering method begins to be utilized in a dental material. However, this alumina comprises grains of 2 μm or less, and even when flexural strength is from 600 to 800 MPa, fracture toughness was merely 3.5 $MPa \cdot m^{0.5}$ or less.

The sintered body of the present invention is a sintered body having high translucency, flexural strength of 350 MPa or more and further 600 MPa or more, and fracture toughness of 4.5 $MPa \cdot m^{0.5}$ or more, in combination.

A bracket requires resistance force withstanding torsional stress received from an orthodontic wire, that is, so-called torque strength. The degree of freedom of design planning of a bracket is increased with increasing resistance force, and complicated design such as small design or self-ligation which does not give uncomfortable feeling to patients is possible. Such torque strength is determined by fracture toughness, rather than flexural strength, of a material. The bracket comprising—the sintered body of the present invention shows high torque strength, and nonconventional new design of the bracket is possible.

A material for repairing dental prosthesis, such as crown or bridge, requires resistance to fracture by clenching stress and translucency for exhibiting sensuousness close to natural tooth. An alumina sintered body is utilized in this use. However, fracture toughness of the conventional alumina is from about 3 to 4 $MPa \cdot m^{0.5}$, and translucency is poor. The sintered body of the present invention has markedly high fracture toughness and high translucency in combination, and therefore can be used as a material for dental prosthesis, in particular, a material of multi-connection bridge or the like that requires high fracture resistance. In recent years, crown, bridge and the like are produced by processing a sintered body with CAD-CAM system, and this sintered body is called a mill blank. The sintered body of the present invention can extremely suppress the generation of chipping or crack in the processing, and constitutes an excellent mill blank.

The alumina sintered body of the present invention has high translucency, and additionally high toughness and high strength. Therefore, when used as a dental material such as an orthodontic bracket or a mill blank for dental prosthesis, the material has high sensuousness based on translucency, and high processability and reliability based on high toughness and high strength.

The alumina sintered body of the present invention not only improves reliability of the conventional uses, but enables new uses such as ceramic self-ligation bracket or three or more multi-connection bridge. Furthermore, it can be used in other uses such as a high pressure sodium lamp tube or a metal halide lamp tube.

The present invention is specifically described below by the Examples and the Comparative Examples, but the invention is not limited to those Examples.

Evaluation methods of the sintered body of the present invention are described below.

(1) Average Aspect Ratio and Average Long Axis Length

A sintered body was mirror-polished, followed by thermal etching, and a scanning electron microgram was obtained. An average aspect ratio and an average long axis length were calculated by an image analyzer of this photograph. The maximum length of each grain was adopted as a long axis length. The shortest distance parallel to the long axis was adopted as a short axis length. A value obtained by dividing the long axis length by the short axis length was adopted as an aspect ratio. An average of the aspect ratios of all grains measured was adopted as an average aspect ratio. An average of a long axis length of each grain was adopted as an average long axis length. The number of grains measured was 100 or more.

(2) Fracture Toughness

A fracture toughness test was based on "Fracture toughness test method of fine ceramics" of JIS R1607, and the fracture toughness was measured by SEPB method.

(3) Flexural Strength

A flexural test was based on "Flexural strength test method of fine ceramics" of JIS R1601, and the flexural strength was measured by a three-point flexural test. An average value of ten measurements was adopted.

(4) All Light Transmittance

All light transmittance was measured by a double beam-system spectrophotometer (V-650 Model, manufactured by JASCO Corporation) based on "Test method of optical characteristics of plastics" of JIS K7105 and "Test method of all light transmittance of plastics and transparent materials" of JIS K7361-1. A measurement sample used was a sample obtained by processing a sintered body to a thickness of 1 mm and mirror polishing both sides to a surface roughness Ra=0.02 µm or less. Light emitted from a light source (deuterium lamp and halogen lamp) was passed through a sample and scattered, and all light transmission amount was measured using an integrating sphere. A measurement wavelength region was from 200 to 800 nm, and all light transmittance in the present invention was a transmittance at a wavelength of 600 nm in a visible light region.

(5) Torque Strength Measurement Evaluation

Torque strength was measured using a torque tester and a bracket sample adhered to a pedestal. 0.018×0.025 inch Co—Cr alloy wire was mounted on a slot of a bracket. The bracket was rotated to break together with the pedestal in a state of fixing the wire, and torque strength was deduced from the broken stress. The torque strength was measured for five samples, and its average value was adopted.

EXAMPLES 1 TO 12

Sodium metasilicate was added to a high purity alumina powder (purity: 99.99% or more, manufactured by Taimei Chemicals Co., Ltd.) in an amount of 50, 100 or 200 ppm, followed by mixing with a ball mill, to prepare a starting powder. Analytical values of impurities of the high purity alumina powder are shown in Table 1. In the high purity alumina powder itself, the total amount of components corresponding to impurities was 20 ppm or less, and components not shown in Table 1 were lower than the detection limit (<1 ppm).

Using a uniaxial press apparatus and a mold, pressure of 50 MPa was applied to form a plate-like molded article having 40 mm×50 mm and a thickness of 5 mm. The molded article was placed in a rubber mold, and pressure of 200 MPa was applied with a cold isotactic press apparatus to mold. The molded article was sintered at 1,300° C. for 2 hours in the atmosphere to obtain a primary sintered body. The primary sintered body was treated at a temperature of from 1,300 to 1,550° C. under a pressure of 150 MPa for 1 hour in an argon gas by HIP apparatus.

Figure 3:
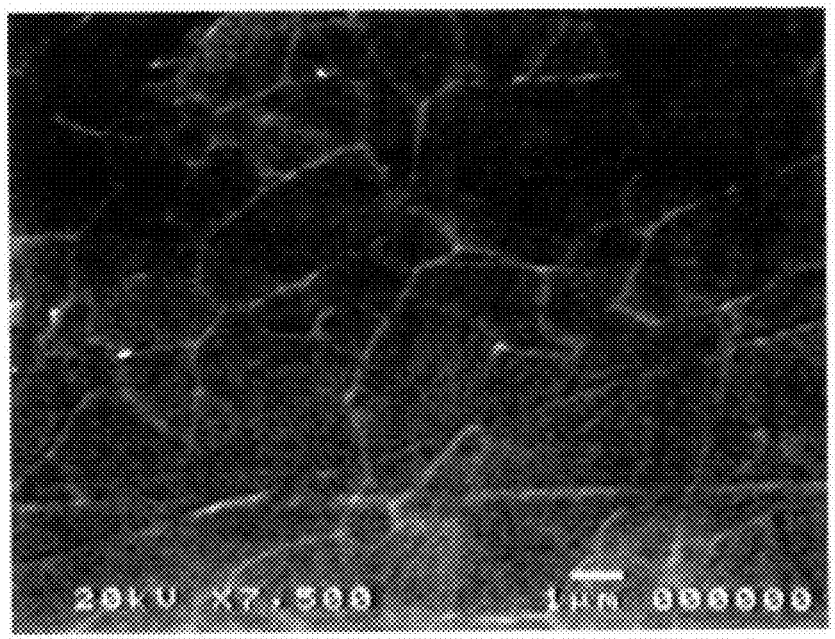
FIG. 3 is SEM photograph of the sintered body (Sample No. 1-3) of the present invention.
Figure 4:
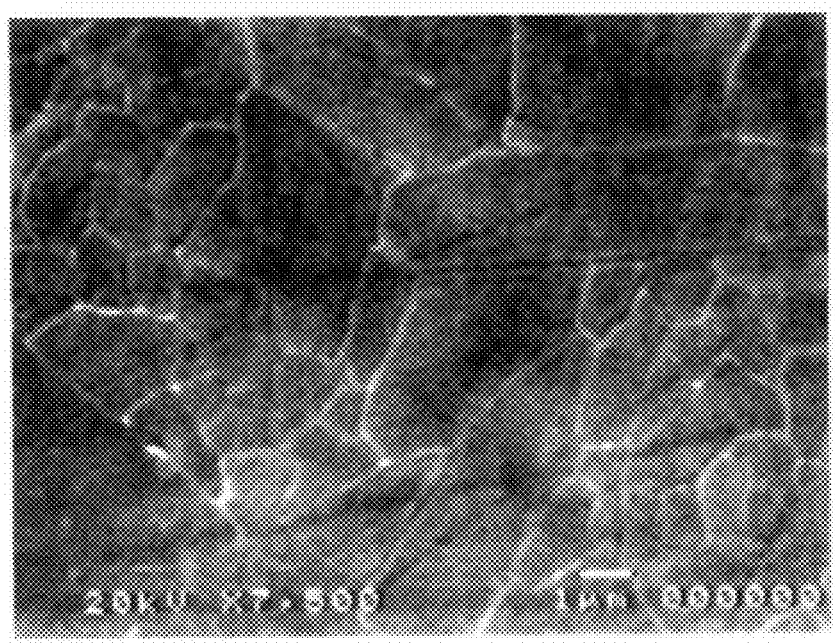
FIG. 4 is SEM photograph of the sintered body (Sample No. 1-7) of the present invention.

The results of aspect ratio, average long axis length, fracture toughness, flexural strength, and all light transmittance (sample thickness: 1 mm, wavelength: 600 nm) are shown in Table 2. Composition analytical values of additives in the sintered body are shown in Table 3. By the presence of oxides of additives, highly translucent sintered body having extremely high fracture toughness value was obtained. Representative examples of the sintered body texture are shown in FIGS. 3 and 4.

TABLE 1

| $Na_2O$ (ppm) | $K_2O$ (ppm) | CaO (ppm) | $SiO_2$ (ppm) | Total (ppm) |
|---|---|---|---|---|
| 6 | 2 | 2 | 6 | 16 |

TABLE 2

| Example (Sample No.) | Amount charged (ppm) | HIP temperature (° C.) | Aspect ratio | Average long axis length (µm) | Fracture toughness (M · Pa · m$^{0.5}$) | Flexural Strength (MPa) | All light transmittance (%) |
|---|---|---|---|---|---|---|---|
| Example 1 (1-1) | 50 | 1350 | 1.60 | 0.85 | 4.5 | 612 | 64.3 |
| Example 2 (1-2) | 50 | 1400 | 1.55 | 1.24 | 5.2 | 553 | 69.2 |
| Example 3 (1-3) | 50 | 1450 | 1.75 | 3.10 | 6.6 | 496 | 69.6 |
| Example 4 (1-4) | 50 | 1475 | 2.08 | 4.96 | 8.1 | 416 | 70.1 |
| Example 5 (1-5) | 100 | 1350 | 1.70 | 0.86 | 4.5 | 550 | 64.2 |
| Example 6 (1-6) | 100 | 1400 | 1.75 | 1.27 | 4.9 | 501 | 68.7 |
| Example 7 (1-7) | 100 | 1450 | 2.07 | 3.16 | 6.4 | 428 | 69.8 |

TABLE 2-continued

| Example (Sample No.) | Amount charged (ppm) | HIP temperature (° C.) | Aspect ratio | Average long axis length (μm) | Fracture toughness (M · Pa · m$^{0.5}$) | Flexural Strength (MPa) | All light transmittance (%) |
|---|---|---|---|---|---|---|---|
| Example 8 (1-8) | 100 | 1475 | 2.58 | 6.11 | 7.6 | 396 | 70.3 |
| Example 9 (1-9) | 200 | 1350 | 1.85 | 1.23 | 4.5 | 520 | 62.0 |
| Example 10 (1-10) | 200 | 1400 | 1.90 | 1.40 | 5.0 | 478 | 65.3 |
| Example 11 (1-11) | 200 | 1450 | 2.16 | 3.21 | 6.7 | 416 | 62.0 |
| Example 12 (1-12) | 200 | 1475 | 2.71 | 4.45 | 8.0 | 368 | 64.3 |

COMPARATIVE EXAMPLES 1 TO 3

Figure 5:
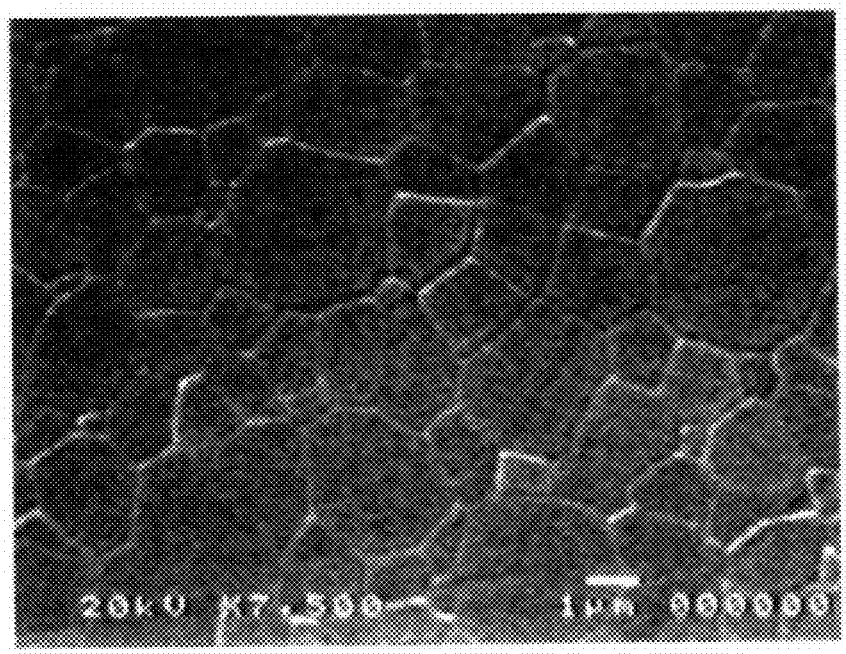
FIG. 5 is SEM photograph of the sintered body (Sample No. 1-15) of the Comparative Example.

Using a high purity alumina powder (purity: 99.99% or more, manufactured by Taimei Chemicals Co., Ltd.) having added thereto 500 ppm of MgO, a sintered body was produced by the sample production method described in Example 1, and aspect ratio, average long axis length, fracture toughness by SEPB method, three-point flexural strength and all light transmittance of the sintered body were measured. The results are shown in Table 4. Composition analysis of additives in the sintered body is shown in Table 5. Representative example of the sintered body texture is shown in FIG. 5.

TABLE 3

| Example (Sample No.) | Amount charged (ppm) | Na$_2$O (ppm) | K$_2$O (ppm) | CaO (ppm) | SiO$_2$ (ppm) | Total (ppm) |
|---|---|---|---|---|---|---|
| Example 3 (1-3) | 50 | 23 | 5 | 6 | 24 | 58 |
| Example 7 (1-7) | 100 | 42 | 5 | 6 | 41 | 94 |
| Example 11 (1-11) | 200 | 128 | 5 | 5 | 60 | 198 |

TABLE 4

| Comparative Example (Sample No.) | Powder | HIP temperature (° C.) | Aspect ratio | Average long axis length (μm) | Fracture toughness (M · Pa · m$^{0.5}$) | Flexural strength (MPa) | All light transmittance (%) |
|---|---|---|---|---|---|---|---|
| Comparative Example 1 (1-13) | No addition | 1300 | 1.44 | 0.31 | 3.3 | 761 | 65.0 |
| Comparative Example 2 (1-14) | No addition | 1350 | 1.42 | 0.90 | 3.5 | 700 | 65.3 |
| Comparative Example 3 (1-15) | MgO 500 ppm added | 1500 | 1.22 | 2.22 | 3.2 | 530 | 69.5 |

TABLE 5

| Comparative Example (Sample No.) | Na$_2$O (ppm) | K$_2$O (ppm) | CaO (ppm) | SiO$_2$ (ppm) | Total (ppm) |
|---|---|---|---|---|---|
| Comparative Example 1 (1-13) | 7 | 2 | 3 | 7 | 19 |
| Comparative Example 3 (1-15) | 6 | 3 | 4 | 5 | 18 |

EXAMPLES 13 TO 18

Using a high purity alumina powder (purity: 99.9%, specific surface area: 14.6 m$^2$/g, manufactured by Taimei Chemicals Co., Ltd.) and two kinds of wax type thermoplastic resins containing Na$_2$O, SiO$_2$ and the like, the resin was mixed with the powder in a proportion of 100 g per 500 g of the powder to prepare an alumina compound.

The alumina compound was molded in a plate shape by an injection molding machine. The molded article was heated to 600° C. to burn out resins, and fired at 1,300° C. for 2 hours in the atmosphere to obtain a primary sintered body. The primary sintered body was subjected to HIP treatment under a pressure of 150 MPa in an argon gas atmosphere by an HIP apparatus. Compositional analysis, density measurement, average aspect measurement, average long axis length measurement, flexural strength measurement, fracture toughness measurement and all light transmittance measurement were conducted to the sintered body sample obtained. The results are shown in Tables 6 to 8.

TABLE 6

| | Na$_2$O (ppm) | SiO$_2$ (ppm) | CaO (ppm) | K$_2$O (ppm) | Total amount of impurities (ppm) |
|---|---|---|---|---|---|
| A | 45 | 28 | 10 | 6 | 89 |
| B | 16 | 9 | 4 | 4 | 33 |

TABLE 7

| Example (Sample No.) | Resin component | Primary sintering temperature (° C.) | HIP treatment temperature (° C.) | Average long axis length (μm) | Average aspect ratio |
|---|---|---|---|---|---|
| Example 13 (2-1) | A | 1300 | 1500 | 3.95 | 2.21 |
| Example 14 (2-2) | A | 1300 | 1475 | 2.60 | 1.81 |
| Example 15 (2-3) | A | 1300 | 1450 | 1.73 | 1.73 |
| Example 16 (2-4) | A | 1300 | 1425 | 1.68 | 1.66 |
| Example 17 (2-5) | B | 1300 | 1500 | 4.64 | 1.52 |
| Example 18 (2-6) | B | 1300 | 1450 | 3.06 | 1.61 |

TABLE 8

| Example (Sample No.) | Flexural strength (MPa) | Fracture toughness value (MPa·m$^{0.5}$) | All light transmittance (Thickness: 1 mm) (%) |
|---|---|---|---|
| Example 13 (2-1) | 649 | 9.4 | 72.0 |
| Example 14 (2-2) | 760 | 6.1 | 71.5 |
| Example 15 (2-3) | 808 | 4.7 | 74.0 |
| Example 16 (2-4) | 834 | 4.5 | 73.1 |
| Example 17 (2-5) | 659 | 5.5 | 70.2 |
| Example 18 (2-6) | 692 | 5.0 | 73.5 |

Figure 6:
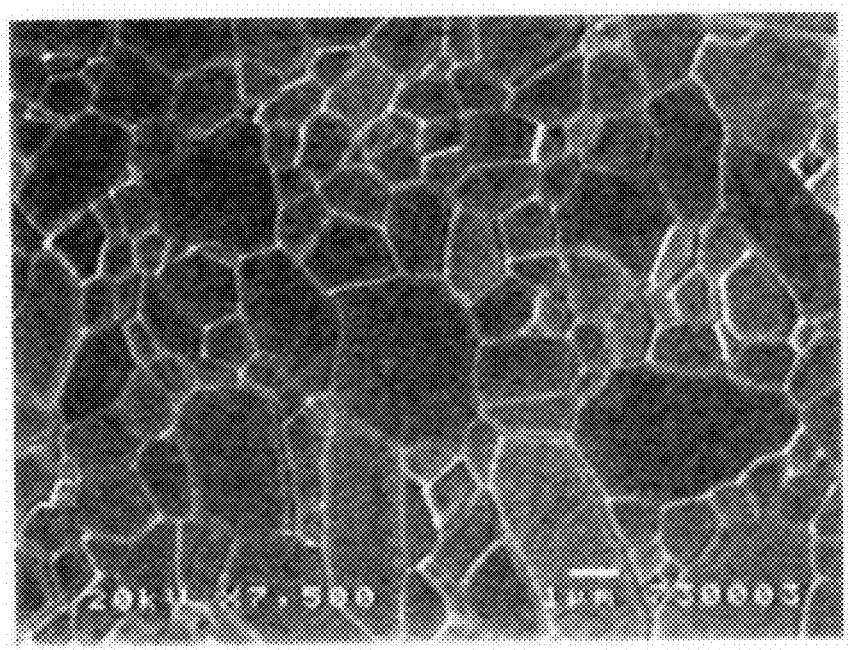
FIG. 6 is SEM photograph of the sintered body (Sample No. 2-3) of the present invention.
Figure 7:
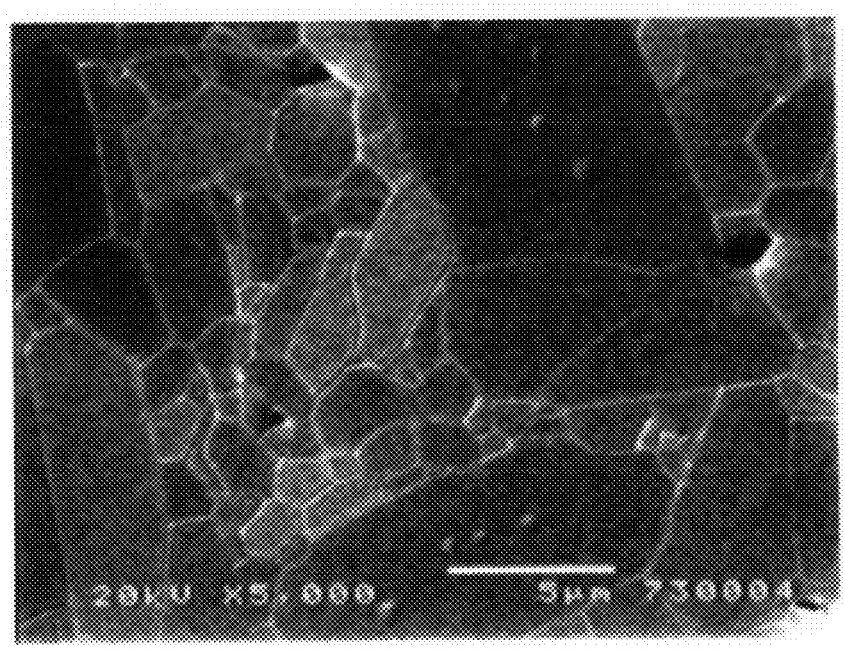
FIG. 7 is SEM photograph of the sintered body (Sample No. 2-1) of the present invention.

In the alumina sintered body having the total amount of oxides added of from 30 to 100 ppm, the average aspect ratio is from 1.52 to 2.21 by the HIP treatment at from to 1,500° C., and sintered bodies having all light transmittance exceeding 70% were obtained. Alumina sintered bodies having excellent mechanical characteristics of fracture toughness value of 4.5 MPa·m$^{0.5}$ or more and flexural strength of 600 MPa or more were obtained. Examples of the sintered body texture are shown in FIGS. 6 and 7.

COMPARATIVE EXAMPLES 4 AND 5

Figure 8:
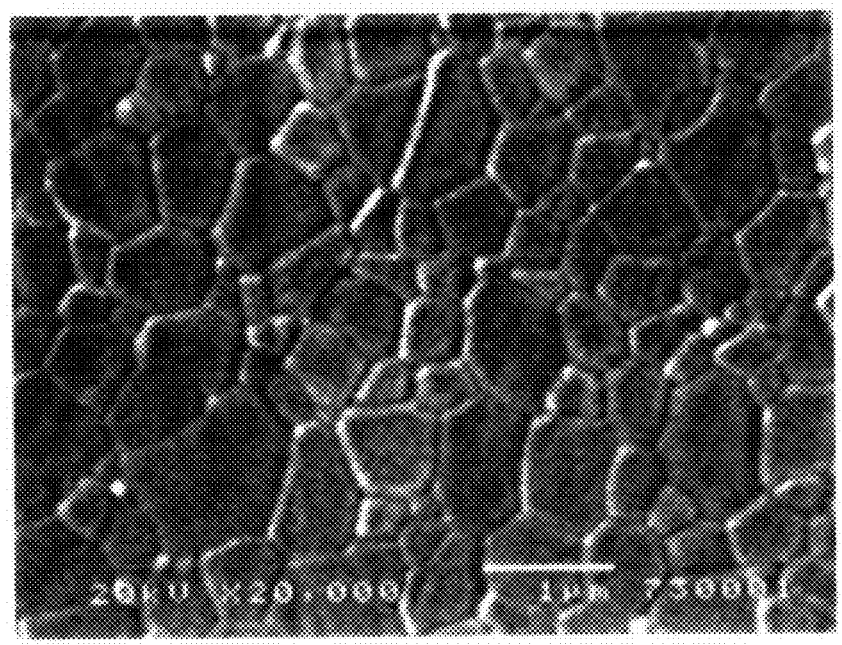
FIG. 8 is SEM photograph of the sintered body (Sample No. 2-8) of the Comparative Example.
Figure 9:
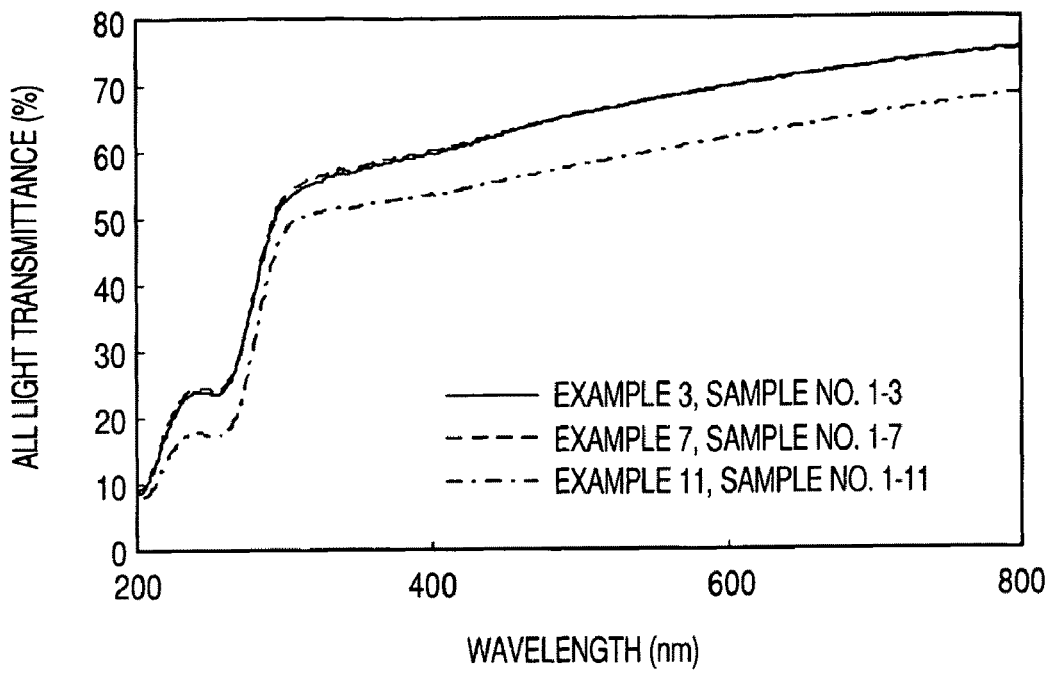
FIG. 9 is all light transmittance curve of the sintered body of the present invention.

A primary sintered body produced by the sample production method described in Example 13 was subjected to HIP treatment at 1,250° C. and 1,300° C. that are lower than the HIP temperature described in Example 13. The same measurement as in the Examples was conducted to the sintered body obtained. The results are shown in Tables 9 and 10. The example of the sintered body texture is shown in FIG. 8.

TABLE 9

| Comparative Example (Sample No.) | Resin component | Primary sintering temperature (° C.) | HIP treatment temperature (° C.) | Average long axis length (μm) | Average aspect ratio |
|---|---|---|---|---|---|
| Comparative Example 4 (2-7) | A | 1300 | 1250 | 0.88 | 1.31 |
| Comparative Example 5 (2-8) | A | 1300 | 1300 | 0.95 | 1.42 |

TABLE 10

| Comparative Example (Sample No.) | Flexural strength (MPa) | Fracture toughness value (MPa·m$^{0.5}$) | All light transmittance (Thickness: 1 mm) (%) |
|---|---|---|---|
| Comparative Example 4 (2-7) | 918 | 3.2 | 72.9 |
| Comparative Example 5 (2-8) | 1017 | 3.3 | 65.1 |

When the HIP treatment temperature is decreased, the average aspect ratio does not exceed 1.5, and due to its texture form, only an alumina sintered body having low fracture toughness value was obtained.

EXAMPLES 19 TO 21 AND COMPARATIVE EXAMPLE 6

Figure 10:
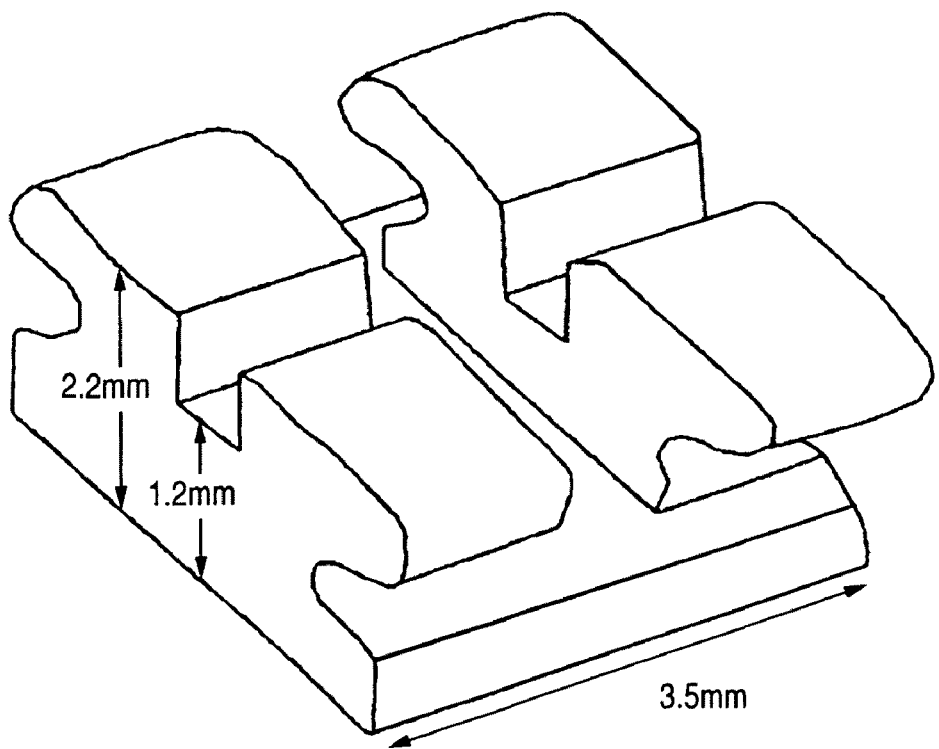
FIG. 10 is one example of a translucent alumina orthodontic bracket shape of the present invention.

The same compound A produced in Example 13 was molded into the desired bracket shape shown in FIG. 10 by an injection molding machine. The molded article was heated to 600° C. to burn out resins, and then fired at 1,300° C. for 2 hours in the atmosphere. The sintered body was subjected to HIP treatment under the same conditions as in Example 13. The bracket obtained showed translucency in the same degree as in the samples of the Examples. 0.018×0.025 inch Co—Cr alloy wire was mounted on a slot of a bracket fixed on a sample table. The bracket was rotated in a state of fixing the wire to measure torque strength. The torque strength was measured for five samples, and its average value was adopted. The results are shown in Table 11.

TABLE 11

| Example/ Comparative Example (Sample No.) | Same conditions Sample No. | HIP temperature (° C.) | Torque strength (kgf·cm) |
|---|---|---|---|
| Example 19 (3-1) | (2-1) | 1500 | 0.65 |
| Example 20 (3-2) | (3-2) | 1475 | 0.63 |
| Example 21 (3-3) | (3-3) | 1450 | 0.60 |
| Comparative Example 6 (3-4) | (3-4) | 1300 | 0.46 |

It was seen from the results of Table 11 and Table 8 described in Example 2 that average torque strength of a bracket is increased with the increase of fracture toughness value. It could be confirmed that an orthodontic bracket having high torque strength while maintaining high translucency is realized from an alumina sintered body texture in the present invention.

While the invention has been described in detail and with reference to specific embodiments thereof, it will be apparent to one skilled in the art that various changes and modifications can be made therein without departing from the spirit and scope thereof.

This application is based on a Japanese patent application filed on Oct. 30, 2007 (Application No. 200-7-281926), the contents thereof being herein incorporated by reference.

What is claimed is:

1. A translucent alumina sintered body
comprising sintered crystal grains having a slender plate and/or columnar shape,
containing 99.95 wt % or more of aluminium oxide, and at least one selected from the group consisting of silicon oxide, boron oxide, phosphorus oxide, germanium oxide, Group 1A alkali metal oxides, and Group 2A alkaline earth metal oxides other than MgO in the total amount of from 20 to 400 ppm and having fracture toughness of 4.5 MPa·m$^{0.5}$ or more, flexural strength of 350 MPa or more, and all light transmittance of a sample having a thickness of 1 mm to a visible light having a wavelength of 600 nm, of 60% or more.

2. The translucent alumina sintered body as claimed in claim 1, wherein the sintered crystal grains are slender plate shape or columnar shape each having an average aspect ratio of 1.5 or more and an average long axis length of 15 μm or less, or a mixture of both the slender plate shape and columnar shape grains.

3. A dental material using the translucent alumina sintered body as claimed in claim 1.

4. A dental material using the translucent alumina sintered body as claimed in claim 2.

5. An orthodontic bracket or a mill blank for dental prosthesis comprising the translucent alumina sintered body of claim 1.

6. An orthodontic bracket or a mill blank for dental prosthesis comprising the translucent alumina sintered body of claim 2.

* * * * *